United States Patent
Schippers et al.

(10) Patent No.: US 10,729,921 B2
(45) Date of Patent: Aug. 4, 2020

(54) GANTRY FOR PARTICLE THERAPY AS AN ARM ROTATING IN THE LONGITUDINAL PLANE

(71) Applicant: PAUL SCHERRER INSTITUT, Villigen PSI (CH)

(72) Inventors: Jacobus Maarten Schippers, Remigen (CH); Alexander Gerbershagen, Meyrin (CH)

(73) Assignee: Paul Scherrer Institut, Villigen (CH)

(*) Notice: Subject to any disclaimer, the term of this patent is extended or adjusted under 35 U.S.C. 154(b) by 0 days.

(21) Appl. No.: 16/324,638

(22) PCT Filed: Jun. 20, 2017

(86) PCT No.: PCT/EP2017/065100
§ 371 (c)(1),
(2) Date: Feb. 11, 2019

(87) PCT Pub. No.: WO2018/028863
PCT Pub. Date: Feb. 15, 2018

(65) Prior Publication Data
US 2019/0184201 A1 Jun. 20, 2019

(30) Foreign Application Priority Data
Aug. 9, 2016 (EP) .................................... 16183296

(51) Int. Cl.
*A61N 5/10* (2006.01)
*G21K 5/10* (2006.01)

(52) U.S. Cl.
CPC ......... *A61N 5/1082* (2013.01); *A61N 5/1028* (2013.01); *A61N 5/1081* (2013.01);
(Continued)

(58) Field of Classification Search
CPC .. A61N 5/1081; A61N 5/1082; A61N 5/2083; A61N 2205/1087; A61N 2205/109
See application file for complete search history.

(56) References Cited

U.S. PATENT DOCUMENTS

| 5,345,632 A | 9/1994 | Langenaeken et al. |
|---|---|---|
| 9,302,123 B2 | 4/2016 | Amelia |

(Continued)

FOREIGN PATENT DOCUMENTS

| EP | 2886158 A1 | 6/2015 |
|---|---|---|
| EP | 3167933 A1 | 5/2017 |

(Continued)

*Primary Examiner* — Eliza W Osenbaugh-Stewart
(74) *Attorney, Agent, or Firm* — Laurence Greenberg; Werner Stemer; Ralph Locher

(57) ABSTRACT

A system for particle beam therapy has an adjustable gantry for beam delivery to a patient site. The gantry has a beam coupling section, a first beam bending section with beam deflection and/or focusing magnets. A beam transport section receiving the particle beam from the first beam bending section and guiding the particle beam to a second beam bending section. The beam exits at a window of a beam nozzle. A patient table/chair is rotatable in the horizontal plane or in a plane being parallel to the horizontal plane and optionally being adjustable vertically. The gantry is supported by a tilting mechanism allowing the gantry to be tilted vertically by an angle $\Phi1\varepsilon[-90°; +90°]$. A rotation mechanism is disposed in a way that the second beam bending section and the beam nozzle are rotatable by an angle $\Phi2\varepsilon[-180°; +180°]$ around a direction given by the angle $\Phi1$.

10 Claims, 4 Drawing Sheets

(52) U.S. Cl.
CPC .............. *G21K 5/10* (2013.01); *A61N 5/1031* (2013.01); *A61N 2005/1087* (2013.01)

(56) References Cited

U.S. PATENT DOCUMENTS

| | | | |
|---|---|---|---|
| 2003/0141460 A1* | 7/2003 | Kraft | A61N 5/10 250/492.1 |
| 2007/0051904 A1* | 3/2007 | Kaiser | A61N 5/10 250/492.1 |
| 2011/0150186 A1 | 6/2011 | Ziegler et al. | |
| 2014/0357930 A1* | 12/2014 | Amelia | A61N 5/1081 600/1 |

FOREIGN PATENT DOCUMENTS

| | | |
|---|---|---|
| JP | H05168623 A | 7/1993 |
| JP | H06214100 A | 8/1994 |
| JP | 2001178834 A | 7/2001 |
| JP | 2015500719 A | 1/2015 |
| WO | 0074779 A1 | 12/2000 |
| WO | 2013149945 A1 | 10/2013 |

\* cited by examiner a)

b)

a)

b)

GANTRY FOR PARTICLE THERAPY AS AN ARM ROTATING IN THE LONGITUDINAL PLANE

BACKGROUND OF THE INVENTION

Field of the Invention

The present invention relates to a gantry for particle therapy.

In proton therapy and ion therapy often use is made of a gantry to direct the incident beam from the most optimal angle towards the target (usually a tumor) in the patient. A gantry is a beam transport system (usually comprising magnets) mounted on a mechanical structure that can rotate around the patient who is positioned—often lying but in some cases also sitting on a dedicated treatment table/chair located—at the treatment position. Usually, the rotation range of the gantry is a bit more than 360 degrees, but in some gantries also a bit more than only 180 degrees is used to save space and allow accessing the treatment table/chair at any time during the treatment. Examples for typical rotatable gantries used for proton therapy are disclosed in the European Patent Application 15 194 795.9 and in the International Patent Application WO 2013/149945 A1.

The rotatable gantries deliver the dose to be deposited into a cancerous tumor volume at pencil beam resolution for various gantry-orientations which enable a precise dose accumulation in this tumor volume coincidently preventing healthy tissue in the surrounding of the tumor volume from damage due to the beam stopping effect which materializes in the so-called Bragg Peak. Nevertheless, these gantries of the form of a C-arm require a considerable space to allow its rotation of a system that involves the weight of ten of tons. At each gantry angle a very accurate positioning of the beam delivery components (in particular the sweeper magnets and the last beam bending magnet(s)) is needed in order to obtain the desired beam characteristics, like the beam energy and beam position and beam direction.

SUMMARY OF THE INVENTION

It is therefore the objective of the present invention to provide a system that replaces the current rotatable gantries for particle beam therapy and that provides a significantly simpler set-up and allowing at least the flexibility in beam delivery known from the prior art gantries. Compared to the currently used rotatable gantries the advantages of the present invention shall also provide a lower weight of the system and a smaller space needed.

This objective is achieved according to the present invention by a system for particle beam therapy, comprising as seen in the flow direction of the particle beam:
a) an adjustable gantry for the beam delivery to a target volume, said gantry comprising:
a1) a beam coupling section for the incoming particle beam; said incoming particle beam being oriented substantially horizontally thereby defining a horizontal plane;
a2) a first beam bending section comprising a number of beam deflection and/or focusing magnets; said first bending section either bending the beam with an adjustable angle into the vertical plane, or with 90 degrees in the horizontal plane, but with the mechanical possibility to rotate with an adjustable angle along the axis of the incoming particle beam;
a3) a beam transport section receiving the particle beam leaving the first beam bending section and guiding the particle beam to a second beam bending section;
a4) the second beam bending section comprising a number of beam deflection magnets and/or beam focusing magnets;
a5) a beam nozzle comprising a window for the exit of the particle beam; and
b) a patient table/chair being rotatable and/or shiftable in the horizontal plane or in a plane being parallel to the horizontal plane and optionally being adjustable vertically,
wherein:
c) the gantry is supported by a tilting mechanism allowing the gantry to be tilted vertically by an angle $\Phi_1$ with respect to the horizontal plane, $\Phi_1 \varepsilon [-90°; +90°]$, wherein the gantry comprises a pivot being disposed in the region of the beam coupling section; and
d) a rotation mechanism being disposed in a way that the second beam bending section and the beam nozzle being rotatable by an angle $\Phi_2$, $\Phi_2 \varepsilon [-180°; +180°]$ around a direction given by the angle $\Phi_1$.

The advantages of this system layout are a reduction of the treatment room footprint with respect to that of a conventional gantry according to the prior art and a very simple mechanical construction to move second beam bending section up and down. Further, it is possible to mount a degrader and/or a beam scanning system in the beam transport section between the first beam bending section and the second beam bending section whereas the scanning system may be mounted in the nozzle downstream of the second beam bending section. Furthermore, compared with conventional gantries two rotational axes allow additional freedom in the choice of how a treatment angle is constructed and how the eventual misalignments can be corrected.

With respect to a geometrical set-up of the system that can be easily implemented and/or maintained, i.e. for quality control, the following basic settings can be chosen:
a) maximum of $\Phi_1$ and $\Phi_2=0°$ lead to a particle beam pointing from the vertical direction downwards to the patient table/chair;
b) minimum of $\Phi_1$ and $\Phi_2=180°$ lead to a particle beam pointing from the vertical direction upwards to the patient table/chair;
c) $\Phi_1=0°$ and $\Phi_2=90°$ lead to a particle beam pointing in the horizontal direction from one side to the patient table/chair; and
d) $\Phi_1=0°$ and $\Phi_2=90°$ and a rotation of the patient table/chair of 180° in the horizontal plane lead to a particle beam pointing in the horizontal direction from the other side to the patient table/chair.

These settings allow to "play" with the beam orientation according to the needs and demands of the therapy plan and to get back easily to one of the position according to the basic settings a) to d). The settings therefore allow an extension of the range of $\Phi_2$ into $[180°; +180°]$ The tilting angle of $\Phi_2$ can preferably range from 0° to +180°, so that the isocenter and the patient table/chair are always at the same side of the gantry. In this way, the footprint of the gantry is minimized.

In order to realize a mechanical set-up that can be controlled in a non-complicated way, the tilting mechanism may comprise a telescope arm or a lifting mechanism based on one or two chains along the lifting arm.

Further, the beam transport section may comprise a telescope section, too. This enables the operator during the tilting to maintain the position in terms of the point (isocenter of the system) of the beam passing through the horizontal plane. Herein, it is suitable when the beam transport section can be adjustable in length in order to compensate the change in the horizontal component of the gantry due to the tilting. In this way, the isocenter will be located on a straight line, perpendicular to the direction of the beam after the first bending section.

At some installations it might not be possible to deliver the particle beam right in the direction required for the first and/or second bending section. It is therefore helpful when the first beam bending section may comprise a set of magnets that also deflect in the horizontal plane. The first bending section itself can also rotate mechanically over an axis that coincides with the incoming beam direction. The combination of the 90 degrees deflection due to the magnetic fields in the first bending section and the mechanical rotation of the first beam bending section defines the gantry's first angle $\Phi_1$. Therefore, the first beam bending section is capable to bend the beam not only in the direction given by the first angle $\Phi_1$ but also into a further direction, i.e. within the horizontal plane in which the beam is delivered after its generation, i.e. in a cyclotron.

In a preferred embodiment the system may additionally comprise a beam spreading system to spread the beam in the lateral direction, which is perpendicular to the direction of the beam leaving the second bending section. The beam spreading system can comprise a scattering system that increases the beam diameter and/or a system of fast deflection magnets that scan the beam in the transversal direction. The beam spreading system can be collated before (upstream of) or behind (downstream of) the second bending section.

Preferred embodiments of the present invention are hereinafter described in more detail with reference to the attached drawings which depict in:

DESCRIPTION OF THE INVENTION

Figure 1:
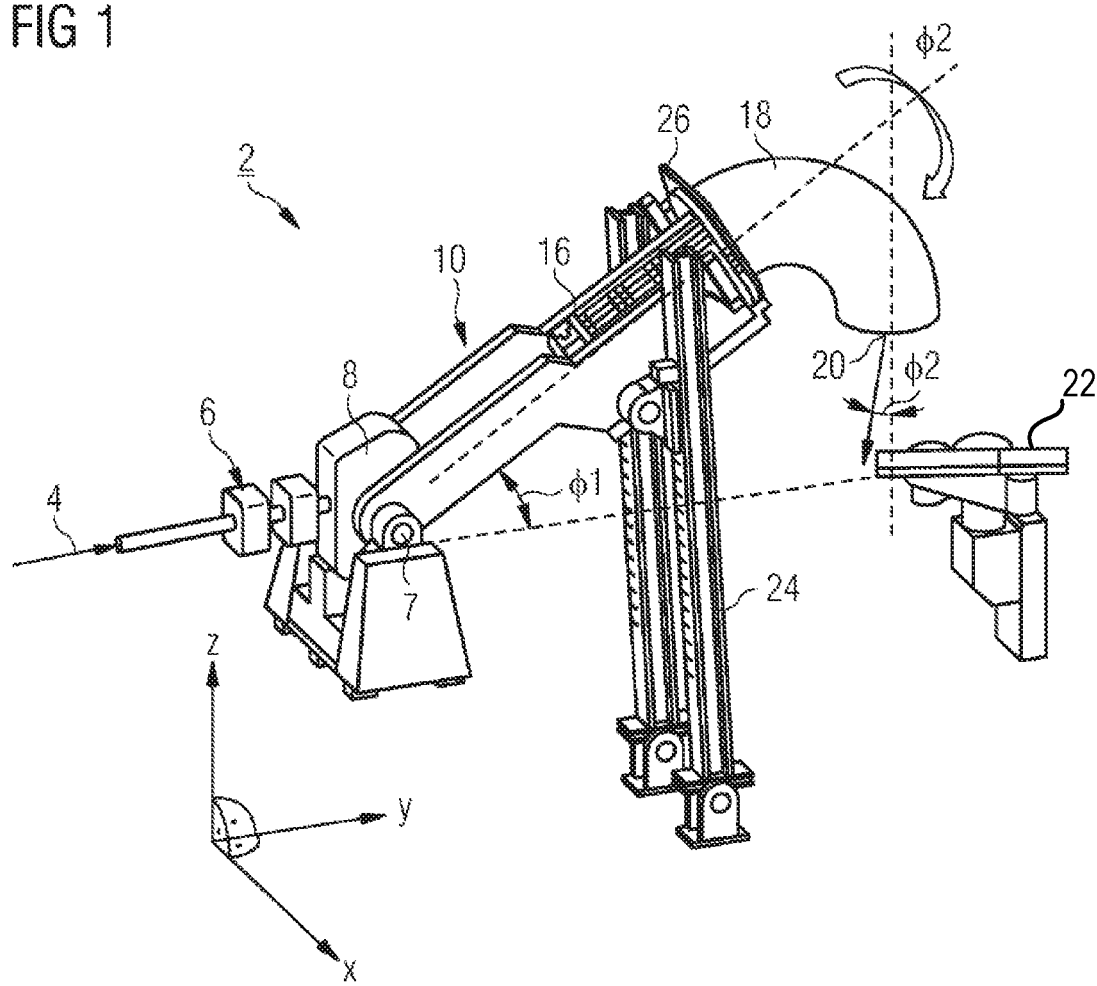
FIG. 1 schematically a perspective view on a first system for particle therapy.
Figure 5:
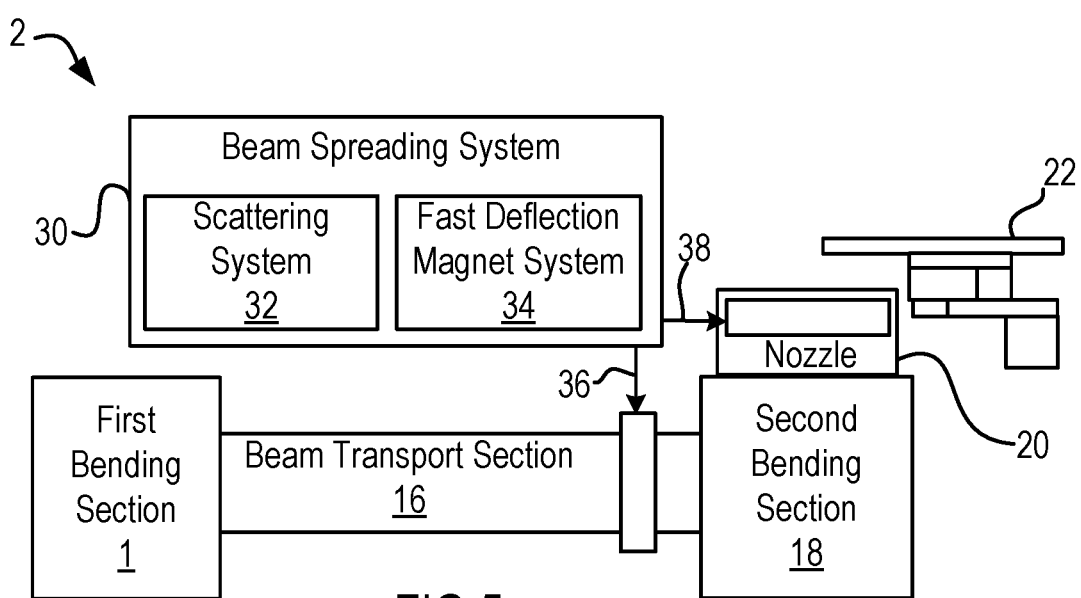
FIG. 5 schematically a simplified block diagram of a system for particle therapy in accordance with another particular embodiment of the invention.

FIG. 1 schematically shows a first system 2 for particle beam therapy delivery. The system 2 comprises for an incoming particle beam 4 a beam coupling section 6 being following by a first bending section 8. In the present example, a gantry 10 is supported by a tilting mechanism 24 allowing the gantry 10 to be tilted vertically (along the z-axis) by an first angle $\Phi_1$, $\Phi_1 \varepsilon [-90°; +90°]$, wherein the gantry 10 comprises the bearing (pivot) 7 being disposed at the entrance of the beam coupling section 6 in order to enable a declination of the complete gantry 10 in the z-direction. The first bending section 8 bends the particle beam 4, such as a proton beam or an ion beam, in the vertical yz plane with an angle $\Phi_1$.

Further, a second bending section 18 and a beam nozzle 20 can be rotated by a rotation mechanism 26 being disposed in a way that the second beam bending section 18 and the beam nozzle 20 being rotatable by an angle $\Phi_2$, $\Phi_2 \varepsilon [-180°; +180°]$ around a direction given by the angle $\Phi_1$, but preferably $\Phi_2 \varepsilon [0°; +180°]$, to limit the footprint of the gantry.

In addition, a beam transport section 16 connecting the first beam bending section 8 to the second bending section 18 can be telescopically adjustable with respect to the length of this beam transport section 16 and allows a variation in length of approximately 0.5 m.

In the shown example, the second beam bending section 18 bends the beam by a fixed angle in the range of 90-135 degrees. This second bending section 18 is rotatable along an axis that approximately equals the direction given by $\Phi_1$ of the unscanned (or central) beam entering the second beam bending section 18. This rotation angle $\Phi_2$ covers at least 180 degrees, between 0 degr. (aiming the beam downwards) and +180 degr (aiming upwards). The appropriate value for $\Phi_2$ is a function of $\Phi_1$. The combination of $\Phi_1$ and $\Phi_2$ determines the incident angle of the beam direction at the patient.

Figure 3:
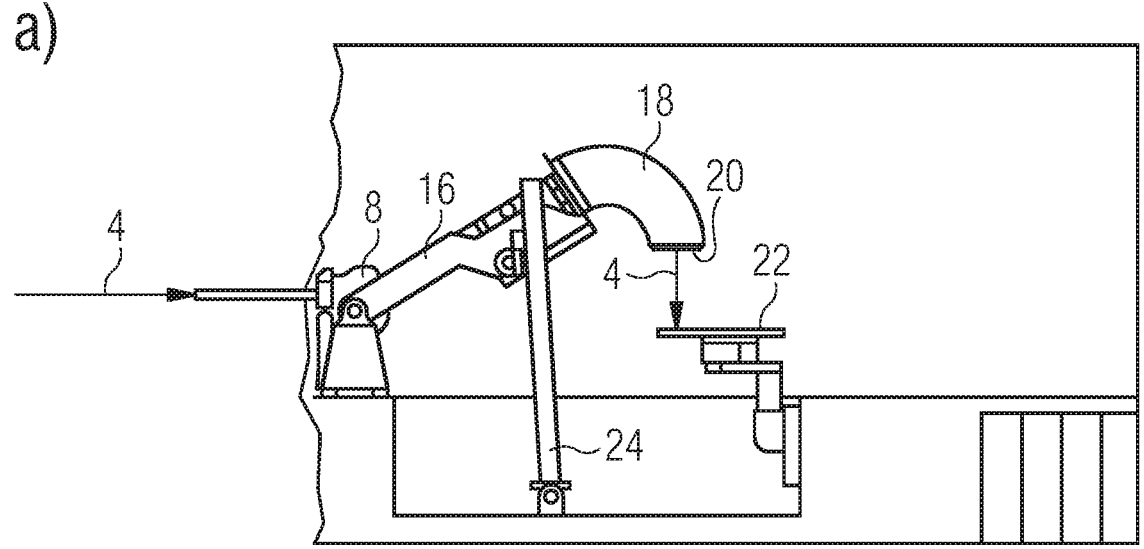
FIG. 3 schematically the position of the system according to FIG. 1 when the particle beam is led vertically downwards (a) and vertically upwards (b)
Figure 3:
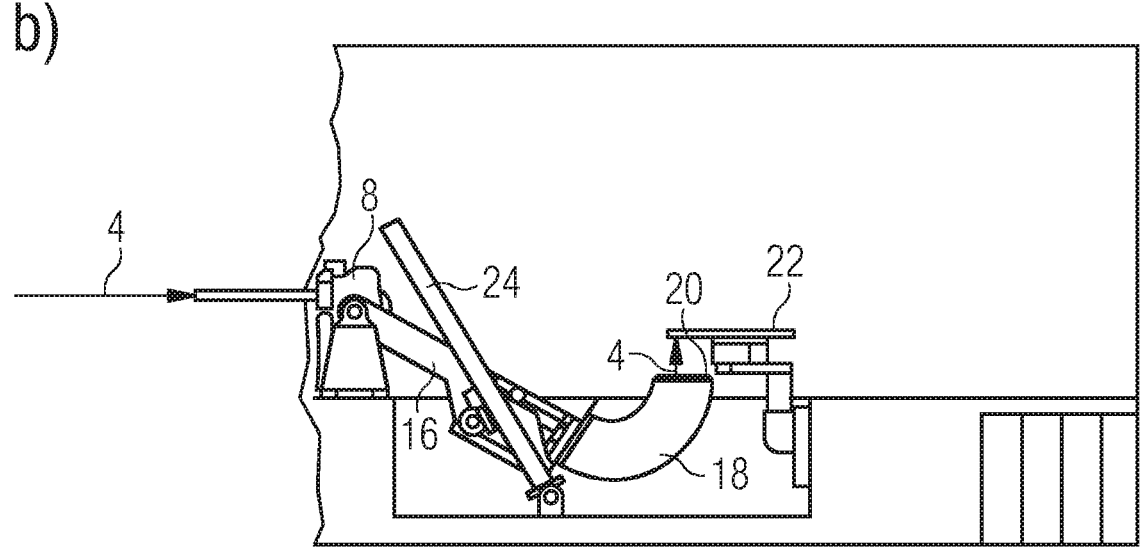

The following three main incident direction can be established:

When $\Phi_1$ is maximal (+) and $\Phi_2=0°$, the particle beam 4 points from the vertical direction down to the patient (see FIG. 3(a)).

When $\Phi_1$ is minimal (−) and $\Phi_2=180°$, the particle beam 4 points in the vertical direction upwards to the patient (see FIG. 3(b)).

Figure 4:
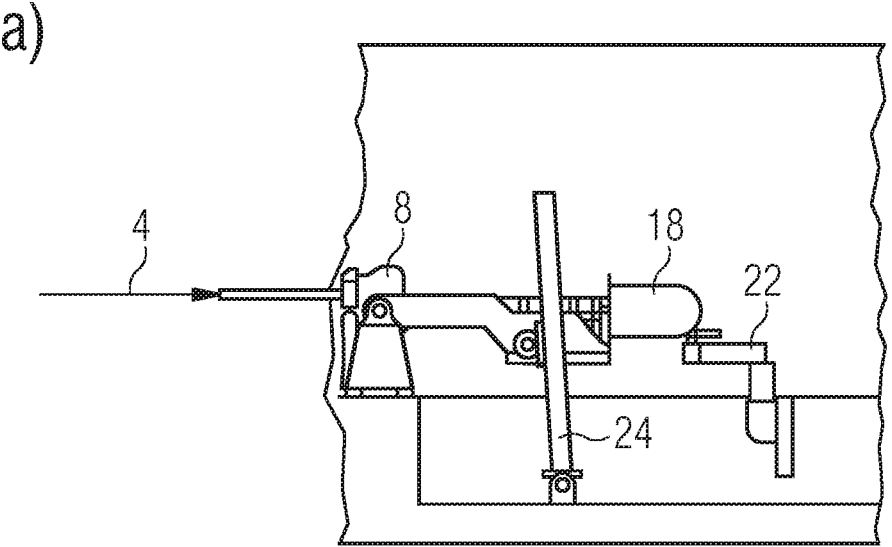
FIG. 4 schematically the position of the system according to FIG. 1 when the particle beam is led horizontally from one side; (a) is a view from the side and (b) is the view from above.
Figure 4:
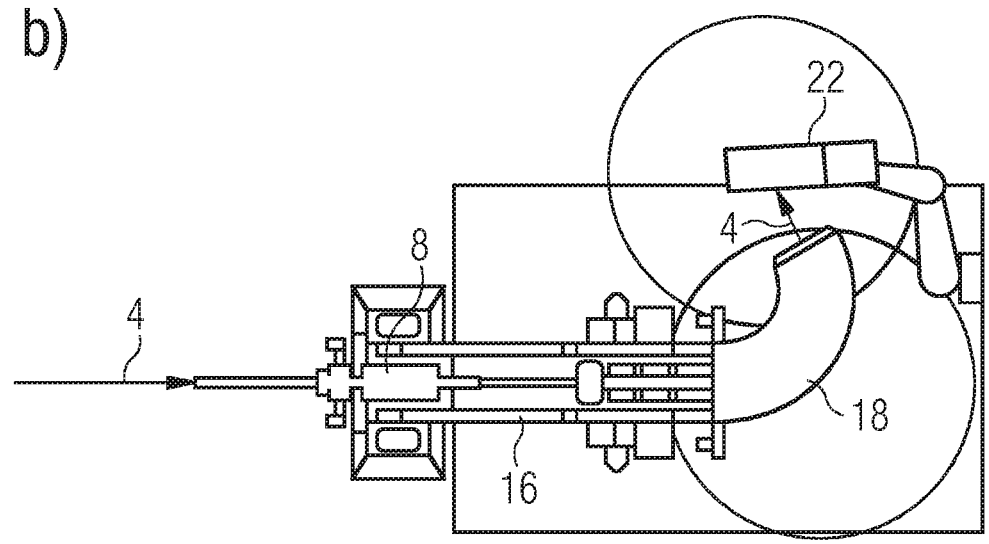

When $\Phi_1=0°$ and $\Phi_2=90°$, the particle beam 4 points in the horizontal direction to the patient (see FIGS. 4 (a) and (b)).

In all orientations small deviations can be added to $\Phi_1$ and $\Phi_2$ by small bending magnets (steering magnets) for fine tuning the incident angle at the patient. A nozzle 20 at the exit of the second bending section 18 can comprise equipment to verify the applied dose and the beam characteristics. A patient table 22 is part of a positioning system that can shift and rotate the patient position in the horizontal plane. The range of this adjustment must be large enough to compensate the motion of the isocenter as a function of $\Phi_1$ and $\Phi_2$.

In order to have a common understanding on the direction, the following definitions are applied:

The horizontal plane is the plane at the height of the particle beam 4 exiting the second beam bending section 18, when $\Phi_1$ is at 0°. This is usually equal to the level of the incoming particle beam 4 at the coupling section 6.

The treatment angle is the angle of the particle beam at the isocenter with respect to the patient orientation and it is determined by a combination of the $\Phi_1$ and $\Phi_2$ and the orientation of the patient table/chair 22.

The isocenter is the location where the beam coming out of the nozzle 20 is crossing the horizontal plane. Typically, $\Phi_2$ is determined by the value of $\Phi_1$ but can be chosen differently in case of exceptional treatment angles or treatment target locations.

The components from the beam transport section 16 until and including the second beam bending section 18 are mounted such that these are always aligned in a mechanical stable or corrected position. The isocenter position is not fixed in space and moves along a curve in the horizontal plane as a function of $\Phi_1$. The shape of this curve depends on whether use is made of the option to have an adjustable (telescopable) length of the beam transfer section 16 which is located between the first beam bending section 10 and the second beam bending section 18. In that case, the length of this beam transport section 16 is a function of $\Phi_1$. This option enables that the isocenter position moves along a straight line in the horizontal plane. This is advantageous for daily checks and in connection to imaging devices that verify the patients positioning with respect to the gantry. However, with appropriate tools for these checks, a curved trajectory of the isocenter position as a function of $\Phi_1$ and $\Phi_2$ is also possible.

The second beam bending section 18 can be designed such that it rotates over a $\Phi_2$ range of >360 degrees or >180 degrees. The 180 degrees version has major advantages, such as a smaller treatment room, less moving range of the patient table 22 and easier rotation construction. This is the version shown in the figures.

Possible advantages of here proposed mechanical layout are:
- a reduction of the treatment room footprint with respect to that of a conventional gantry;
- very simple mechanical construction to move the second beam bending section 18 up and down;
- it is possible to mount a degrader and/or scanning system (sweeper magnets) in the beam transfer section 16 between the first bending section 8 and the second beam bending section 18 or the beam scanning system can be mounted in the nozzle 20 of the second beam bending section 18;
- Compared with conventional gantries the two rotational axes allow one additional degree of freedom in the choice of how a treatment angle is constructed.

In a preferred embodiment, the system 2 may additionally comprise a beam spreading system 30 to spread the beam in the lateral direction, which is perpendicular to the direction of the beam leaving the second bending section 18. The beam spreading system 30 can comprise a scattering system 32 that increases the beam diameter and/or a system of fast deflection magnets 34 that scan the beam in the transversal direction. The beam spreading system 30 can be collated before 36 (upstream of) or behind 38 (downstream of) the second bending section 18.

Figure 2:
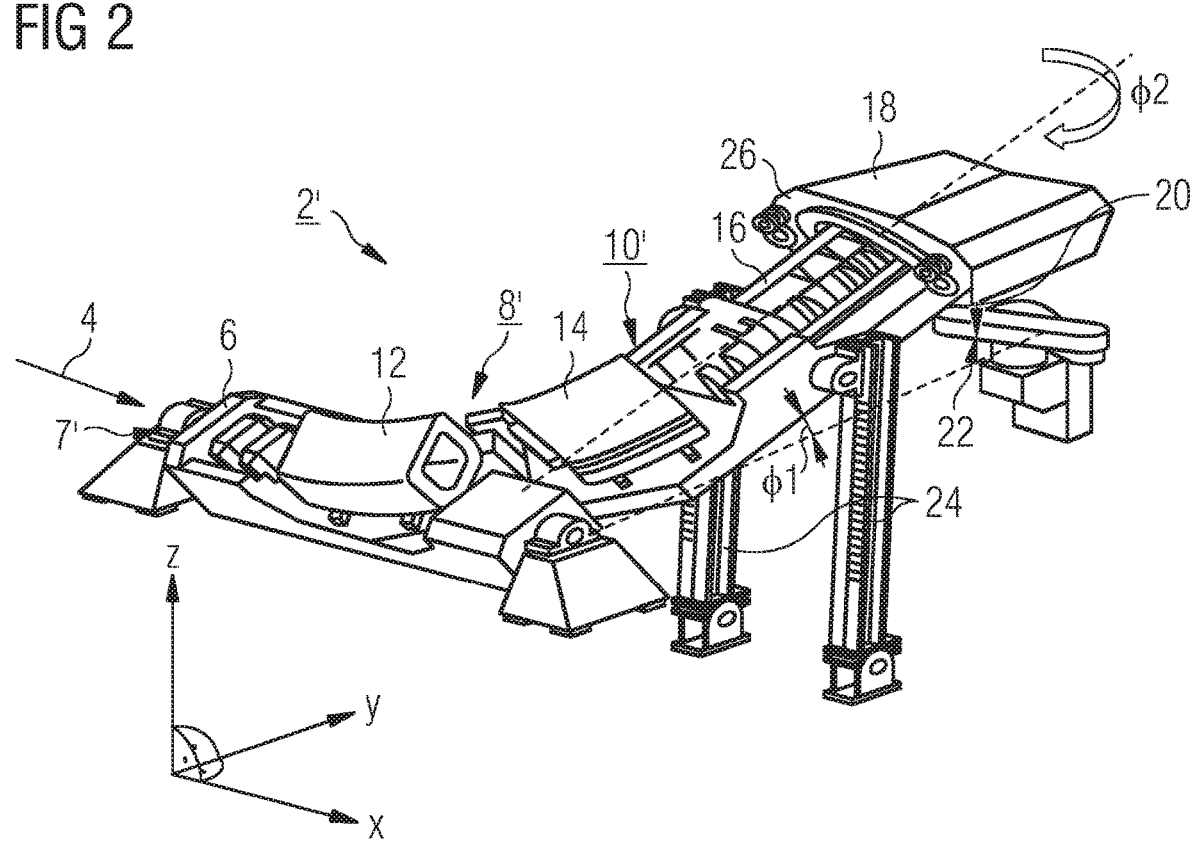
FIG. 2 schematically a perspective view on a second system for the particle therapy that is only slightly amended as compared to FIG. 1.

FIG. 2 schematically shows a system 2' for a therapy using the particle beam 4 that is slightly amended as compared to the system 2. Presently, the particle beam 4 which is generated in a linear accelerator and/or a cyclotron and/or a synchrotron is delivered horizontally along the x-direction to a particle beam gantry—in the following referred to as gantry 10'. Said gantry 10' comprises a coupling section 6. At this coupling section 6, the gantry 10 can be rotated over an angle $\Phi1$ along the x-axis by a rotation bearing 7'. Beside this rotation bearing 7', the coupling section 6 provides beam focusing (collimators) and beam control/diagnosis equipment (not shown in detail) before the particle beam 4 enters into a first bending section 8'. Usually, this first bending section 8' comprises a number of dipole and/or quadrupole magnets 12, 14 which are controlled to bend the particle beam 4 by its magnetic fields into a desired direction. In the present example, the first beam bending section 8' bends the particle beam 4 from the x-direction into the y-direction, so over an angle of 90 degrees in the horizontal plane, if the first bending section 8' is not rotated.

The first beam bending section 8' is followed by the beam transport section 16 receiving the particle beam 4 leaving the first beam bending section 8' and guiding the particle beam 4 to a second beam bending section 18. The beam transport section 16 may comprise further equipment for the beam diagnosis and sweeper magnets as for example known from the WO 2013/149945 A1.

The second beam bending section 18 comprises a number of beam deflection magnets and/or beam focusing magnets in order to deliver the particle beam 4 via the beam nozzle 20 comprising a window for the exit of the particle beam 4 out of the gantry 10' to the patient table 22. The patient table 22 could also comprise a patient chair allowing a patient to be treated in upright position. The patient table/chair 22 is rotatable and/or shiftable in the horizontal plane (given here by the x-and y-axis). Optionally, the patient table/chair may be adjustable vertically, too.

In the present example, the gantry 10' is supported by the tilting mechanism 24 allowing the gantry 10' to be tilted vertically (along the z-axis, in the yz-plane) by a first angle $\Phi_1$, $\Phi_1\varepsilon[-90°; +90°]$, wherein the gantry 10' comprises the rotation bearing (pivot) 7' being disposed at the entrance of the beam coupling section 6 in order to enable a rotation of the complete gantry 10' along the x-axis. Further, the second bending section 18 and the beam nozzle 20 can be rotated by the rotation mechanism 26 being disposed in a way that the second beam bending section 18 and the beam nozzle 20 being rotatable by an angle $\Phi_2$, $\Phi_2\varepsilon[-180°; +180°]$, but preferably $\Phi_2\varepsilon[0°; +180°]$ in order to limit the footprint of the gantry 10') around a direction given by the angle $\Phi_1$.

Typically, the range of the first angle $\Phi_1$ depends on the design of the system 2'. For the system 2', the range of the first angle $\Phi_1$ can typically be between approximately $-40°$ and $+40°$. After the first bending section 8' the out-coming beam 4 is aimed into the $\Phi_1$-direction with respect to the horizontal plane: downwards when $\Phi_1<0$ and upwards when $\Phi_1>0$. Due to the bending in the horizontal plane, the first bending section 8' can be designed such that it can also serve as an energy selection system.

The invention claimed is:

1. A system for particle beam therapy, the system comprising, as seen in a flow direction of a particle beam:
   a) an adjustable gantry for beam delivery to a target volume, said gantry including:
      a1) a beam coupling section for an incoming particle beam, the incoming particle beam being oriented substantially horizontally and defining a horizontal plane;
      a2) a first beam bending section having a plurality of beam deflection and/or focusing magnets, said first beam bending section being configured to either bend the particle beam with an adjustable angle into a vertical plane, or with 90 degrees in the horizontal plane, but with mechanical rotatability about an adjustable angle along an axis of the incoming particle beam;
      a3) a beam transport section disposed to receive the particle beam leaving said first beam bending section and guiding the particle beam to a second beam bending section;
      a4) said second beam bending section having a plurality of beam deflection magnets and/or beam focusing magnets; and
      a5) a beam nozzle formed with a window for an exit of the particle beam; and b) a patient support mounted for rotation and/or shifting in the horizontal plane or in a plane parallel to the horizontal plane;

c) a tilting mechanism supporting said gantry to enable said gantry to be tilted vertically by a tilting angle $\Phi_1$, where $\Phi_1 \varepsilon [-90°; +90°]$, about a pivot disposed in a region of said first beam bending section; and d) a rotation mechanism disposed to enable said second beam bending section and said beam nozzle to rotate by an angle $\Phi_2$, where $\Phi_2 \varepsilon [-180°; +180°]$, around a direction given by the tilting angle $\Phi_1$.

2. The system according to claim 1, comprising the following basic settings:

a) maximum of $\Phi_1$ and $\Phi_2=0°$, leading to a particle beam pointing from the vertical direction downwards to said patient support;

b) minimum of $\Phi_1$ and $\Phi_2=180°$, leading to a particle beam pointing from the vertical direction upwards to said patient support;

c) $\Phi_1=0°$ and $\Phi_2=-90°$, leading to a particle beam pointing in the horizontal direction from one side to said patient support; and d) $\Phi_1=0°$ and $\Phi_2=+90°$, leading to a particle beam pointing in the horizontal direction from an opposite side to said patient support.

3. The system according to claim 1, wherein said tilting mechanism comprises a telescope arm.

4. The system according to claim 1 wherein said beam transport section comprises a telescope section.

5. The system according to claim 4, wherein said beam transport section is adjustable in length in order to compensate for a change in a horizontal component of said gantry due to the tilting angle $\Phi_1$.

6. The system according to claim 1, wherein said first beam bending section comprises a set of magnets in order to deflect the incoming beam into a direction given by the tilting angle $\Phi_1$.

7. The system according to claim 1, which comprises a beam spreading system configured to spread the beam in a lateral direction, which is perpendicular to a direction of the beam leaving said second bending section.

8. The system according to claim 7, wherein said beam spreading system comprises a scattering system configured to increase a beam diameter and/or a system of fast deflection magnets configured to scan the beam in the transversal direction.

9. The system according to claim 8, wherein said beam spreading is collated upstream of or downstream of said second bending section in the flow direction of the beam.

10. The system according to claim 1, wherein a treatment angle of the particle beam at the isocenter with respect to a patient orientation is determined by a combination of the tilting angle $\Phi_1$, the angle $\Phi_2$, and an orientation of the patient support.

* * * * *